(12) United States Patent
Madjarov et al.

(10) Patent No.: US 9,381,101 B2
(45) Date of Patent: Jul. 5, 2016

(54) HYBRID GRAFT FOR THERAPY OF AORTIC PATHOLOGY AND ASSOCIATED METHOD

(71) Applicant: THE CHARLOTTE-MECKLENBURG HOSPITAL AUTHORITY, Charlotte, NC (US)

(72) Inventors: Jeko Metodiev Madjarov, Charlotte, NC (US); Svetozar Madzharov, Sofia (BG)

(*) Notice: Subject to any disclaimer, the term of this patent is extended or adjusted under 35 U.S.C. 154(b) by 398 days.

(21) Appl. No.: 13/833,665

(22) Filed: Mar. 15, 2013

(65) Prior Publication Data

US 2013/0282103 A1    Oct. 24, 2013

Related U.S. Application Data

(60) Provisional application No. 61/636,866, filed on Apr. 23, 2012.

(51) Int. Cl.
*A61F 2/82* (2013.01)
*A61F 2/852* (2013.01)
(Continued)

(52) U.S. Cl.
CPC .................. *A61F 2/852* (2013.01); *A61B 17/11* (2013.01); *A61F 2/06* (2013.01); *A61F 2/064* (2013.01);
(Continued)

(58) Field of Classification Search
CPC ............ A61F 2/064; A61F 2250/0039; A61F 2002/821; A61F 2/82; A61F 2002/823; A61F 2/852; A61F 2/954; A61F 2002/065; A61F 2230/006; A61B 2017/1107; A61B 17/115

USPC .............................. 606/8, 153; 623/1.31, 1.35
See application file for complete search history.

(56) References Cited

U.S. PATENT DOCUMENTS 3,818,511 A * 6/1974 Goldberg et al. ............ 623/1.31
4,366,819 A    1/1983 Kaster
(Continued)

FOREIGN PATENT DOCUMENTS

WO    WO-97/03616 A1    2/1997
WO    WO-2009/046994 A2    4/2009
WO    WO-2011/084559 A2    7/2011

OTHER PUBLICATIONS

Criado, F. J.; "*Aortic Dissection: A 250-Year Perspective*;" Texas Heart Institute Journal, vol. 38, No. 6; pp. 694-700; dated 2011; retrieved on Mar. 20, 2013 from <http:www.ncbi.nlm.nih.gov/pmc/articles/PMC3233335/>.
(Continued)

*Primary Examiner* — Christian Sevilla
*Assistant Examiner* — Seema Mathew
(74) *Attorney, Agent, or Firm* — Smith Moore Leatherwood LLP

(57) ABSTRACT

Vascular devices and methods for addressing aortic pathologies are provided that facilitate hemostasis at the junctions of the ends of the device with the native aorta or other vessels to minimize or eliminate the risk of endoleaks. One or both ends of the device may include inner and outer skirts that are configured to receive a section of native blood vessel therebetween. The outer skirt may be flared in some cases or rolled up prior to placement at and engagement with the blood vessel to provide clearance for joining the blood vessel to the inner skirt of the device, such as via sutures. Once engaged, the outer skirt is disposed such that the blood vessel is between the inner and outer skirts. Devices and associated methods are also described that allow endografts to be deployed and engaged with an end of the device in areas with insufficient landing zones.

11 Claims, 8 Drawing Sheets

(51) Int. Cl.
*A61F 2/06* (2013.01)
*A61B 17/11* (2006.01)

(52) U.S. Cl.
CPC . *A61B 2017/1107* (2013.01); *A61B 2017/1132* (2013.01); *A61F 2002/061* (2013.01); *A61F 2002/065* (2013.01); *A61F 2230/006* (2013.01); *A61F 2230/0067* (2013.01); *A61F 2250/0039* (2013.01)

(56) References Cited

U.S. PATENT DOCUMENTS

| | | | | |
|---|---|---|---|---|
| 4,470,415 | A * | 9/1984 | Wozniak | A61B 17/11 29/447 |
| 4,957,508 | A | 9/1990 | Kaneko et al. | |
| 5,192,289 | A * | 3/1993 | Jessen | A61B 17/11 606/153 |
| 5,562,727 | A | 10/1996 | Turk et al. | |
| 5,591,226 | A * | 1/1997 | Trerotola et al. | 623/1.12 |
| 5,906,641 | A | 5/1999 | Thompson et al. | |
| 5,989,287 | A * | 11/1999 | Yang et al. | 623/1.36 |
| 6,296,661 | B1 | 10/2001 | Davila et al. | |
| 6,348,066 | B1 | 2/2002 | Pinchuk et al. | |
| 6,699,257 | B2 | 3/2004 | Gifford, III et al. | |
| 6,821,295 | B1 | 11/2004 | Farrar | |
| 6,918,925 | B2 | 7/2005 | Tehrani | |
| 7,074,235 | B1 * | 7/2006 | Roy | 623/1.11 |
| 7,112,211 | B2 | 9/2006 | Gifford, III et al. | |
| 8,002,816 | B2 | 8/2011 | Greenberg | |
| 8,333,800 | B2 * | 12/2012 | Bruszewski | A61F 2/07 623/1.13 |
| 2001/0044647 | A1 | 11/2001 | Pinchuk et al. | |
| 2002/0173836 | A1 | 11/2002 | Pinchuk | |
| 2003/0114923 | A1 | 6/2003 | Swanick et al. | |
| 2003/0199967 | A1 * | 10/2003 | Hartley | A61F 2/07 623/1.13 |
| 2004/0249433 | A1 * | 12/2004 | Freitag | A61F 2/95 623/1.11 |
| 2006/0212052 | A1 * | 9/2006 | Shin | A61F 2/82 606/153 |
| 2006/0247761 | A1 * | 11/2006 | Greenberg | A61F 2/07 623/1.16 |
| 2007/0021828 | A1 * | 1/2007 | Krolik | A61F 2/91 623/1.31 |
| 2007/0168013 | A1 | 7/2007 | Douglas | |
| 2009/0264993 | A1 | 10/2009 | Greenan | |
| 2009/0270965 | A1 | 10/2009 | Sinha et al. | |
| 2010/0262171 | A1 * | 10/2010 | Wu | A61B 17/11 606/155 |
| 2011/0106115 | A1 * | 5/2011 | Haselby | A61B 5/076 606/151 |
| 2011/0257731 | A1 * | 10/2011 | Hartley | A61F 2/07 623/1.35 |
| 2014/0277369 | A1 * | 9/2014 | Roeder | A61F 2/07 623/1.13 |
| 2014/0316509 | A1 * | 10/2014 | Corrigan, Jr. | A61F 2/958 623/1.11 |
| 2014/0350660 | A1 * | 11/2014 | Cocks | A61F 2/2418 623/1.16 |

OTHER PUBLICATIONS

Greenberg, R. K., et al.; "*Cardiovascular Surgery- Hybrid Approaches to Thoracic Aortic Aneurysms: The Role of Endovascular Elephant Trunk Completion*;", Circulation vol. 112, No. 17; pp. 2619-2626; dated 2005; retrieved on Mar. 26, 2012 from <http://circ.ahajournals.org/content/112/17/2619.full>.

Hughes, C. G., et al.; "*Surgery for Acquired Cardiovascular Disease—Use of custom Dacron branch grafts for "hybrid" aortic debranching during endovascular repair of thoracic and thoracoabdominal aortic aneurysms*;" The Journal of Thoracic and Cardiovascular Surgery, vol. 136, No. 1; pp. 21-28; dated 2008; retrieved on Mar. 26, 2012 from <http://jtcs.ctsnetjournals.org/cgi/content/full/136/1/21>.

"*GORE® TAG® Thoracic Endoprosthesis: Conformability without Compromise*;" W. L. Gore & Associated; dated Feb. 2012.

"*Hybrid Aortic Arch Surgery: A new endovascular approach provides hope for patients with aneurysms of the aortic arch*;" Healthpoints E-Newsletter; dated Summer 2010; retrieved on Mar. 26, 2012 from <http://www.columbiasurgery.ord/news/healthpoints/2010_summer/p3.html>.

International Search Report and Written Opinion for Application No. PCT/US2013/037734 dated Feb. 3, 2014.

International Search Report for Application No. PCT/US2013/037734; dated Aug. 28, 2013.

* cited by examiner

HYBRID GRAFT FOR THERAPY OF AORTIC PATHOLOGY AND ASSOCIATED METHOD

CROSS-REFERENCE TO RELATED APPLICATIONS

This application claims the benefit of U.S. Provisional Application No. 61/636,866 entitled "Hybrid Graft For Therapy of Aortic Pathology and Associated Method," filed Apr. 23, 2012, the contents of which are incorporated herein in their entirety.

FIELD OF THE INVENTION

The present invention relates generally to methods and apparatuses for therapy of aortic pathology. More specifically, methods and apparatuses are described for treating vascular abnormalities in the aorta in cases where aortic resection is needed. Methods and apparatuses are also described for addressing target sites near clusters of arterial branches, such as in the aortic arch and in the visceral segment of the aorta.

BACKGROUND

Vascular abnormalities can be serious medical conditions that require prompt and effective treatment. An aneurysm, for example, is a bulging or ballooning portion of the wall of a blood vessel, usually an artery, that is the result of a weakened area of the artery wall. As the aneurysm enlarges, the walls of the artery become thinner, and the risk of rupture increases. A ruptured aneurysm can cause severe hemorrhaging, other complications, and death. Weakened walls of the arteries can be hereditary or can be caused by disease, such as arteriosclerosis.

In some cases, a tear may develop in the inner layer of the aorta, and blood may flow through the tear into the middle layer of the aorta, as shown in FIG. 1. This blood flow may cause the inner and middle layers of the aorta to separate and create a false lumen. This is known as a dissection. Dissections can be fatal if the false lumen ruptures the outside aortic wall. Moreover, a dissection may cause malperfusion, which may limit or cut off blood flow through the aorta or its branches to one or more organs.

In such cases, prompt and effective medical attention is necessary to reduce the risk of patient mortality. Conventional methods of treating vascular conditions such as aortic dissections, however, carry with them additional risks to the health of the patient, especially in the elderly.

Accordingly, there is a need for a method and apparatus for treating aortic abnormalities in a way that minimizes the risks to the patient, is reproducible, and is simple to administer.

BRIEF SUMMARY

A device and method are provided in accordance with an example embodiment for treating aortic abnormalities, in particular abnormalities that require resection of a portion of the aorta. In one embodiment, A vascular device for treating a target site within a body lumen is provided, wherein the vascular device is configured for placement between first and second sections of a patient's native blood vessel. The vascular device may include a first end, a second end, and a lumen extending between the first and second ends. The first end may be configured to be attached to the first section of the native blood vessel, while the second end may be configured to be attached to the second section of the native blood vessel. At least one of the first or second ends may comprise an inner skirt and an outer skirt that at least partially surrounds the inner skirt. The inner and outer skirts may be configured to receive a portion of the respective section of the native blood vessel therebetween for attaching the respective end of the vascular device to the respective section of the native blood vessel.

An outer surface of the inner skirt may be configured to be disposed adjacent an inner surface of the respective section of the native blood vessel and an inner surface of the outer skirt may be configured to be disposed adjacent an outer surface of the respective section of the native blood vessel. In some cases, each end of the vascular device may comprise an inner skirt and an outer skirt configured to receive a portion of the respective section of the native blood vessel therebetween for attaching the respective end of the vascular device to the respective section of the native blood vessel. The outer skirt may be longer than the inner skirt in some embodiments.

The inner skirt may be configured to be sutured to the respective section of the native blood vessel and the outer skirt may be configured to promote hemostasis for minimizing endoleaks proximate the respective end. In some embodiments, one of the first or second ends may be configured to receive an endograft therein. Furthermore, each of the inner and outer skirts may extend away from a central axis defined by the vascular device, thereby forming a flare.

In some embodiments, the outer skirt may be configured to be moved between a first position and a second position, wherein in the first position the outer skirt is biased toward a rolled configuration, such that an outer surface of the inner skirt is exposed for receiving the respective section of native blood vessel, and in the second position the outer skirt is biased toward an extended configuration, such that an inner surface of the outer skirt is disposed opposite the outer surface of the inner skirt, thereby engaging the respective section of native blood vessel therebetween. In some cases, in the second position the outer skirt is configured to apply pressure in a direction toward the inner skirt.

In other embodiments, a vascular device for treating a target site within a body lumen may be provided. The device may comprise a primary tubular structure comprising a first end, a second end, and a primary lumen extending between the first and second ends, and a secondary tubular structure disposed within the primary lumen of the primary tubular structure and comprising a secondary lumen. The secondary tubular structure may be configured to receive an endograft via the secondary lumen and may be configured to serve as a landing zone for the endograft. At least a portion of an outer surface of the secondary tubular structure may be spaced from an inner surface of the primary tubular structure and may define a chamber therebetween. Furthermore, at least one debranching limb may extend from a portion of the primary tubular structure in the area of the chamber such that blood is able to flow through each debranching limb via the chamber to a corresponding branch vessel and is able to flow through the secondary lumen to points downstream.

In some cases, a portion of the secondary tubular structure may be integral to the primary tubular structure. At least a portion of the secondary tubular structure may comprise a nitinol mesh. At least one of the first or second ends of the primary tubular structure may comprise an inner skirt and an outer skirt configured to receive a portion of a respective section of a native blood vessel therebetween for attaching the respective end of the primary tubular structure to the respective section of the native blood vessel.

In still other embodiments, a method for positioning a vascular device proximate a target site within a body lumen is provided. A vascular device may initially be provided that includes a primary tubular structure comprising a first end, a second end, and a primary lumen extending between the first and second ends, a secondary tubular structure disposed within the primary lumen of the primary tubular structure and comprising a secondary lumen, wherein at least a portion of an outer surface of the secondary tubular structure is spaced from an inner surface of the primary tubular structure and defines a chamber therebetween, and at least one debranching limb extending from a portion of the primary tubular structure in the area of the chamber. Each debranching limb may be connected to a corresponding branch vessel such that blood is able to flow through each debranching limb via the chamber to the corresponding branch vessel. A damaged portion of the aorta may be resected, wherein a first section and a second section of the native aorta remain in the body lumen. The second end of the primary tubular structure may be connected to the second section of the native aorta such that blood is able to flow through the secondary lumen to points downstream, and the first end of the primary tubular structure may be connected to the first section of the native aorta. Blood may then be allowed to flow from the heart to perfuse the body via the vascular device.

In some cases, the vascular device may comprise a delivery limb extending from the primary tubular structure. The delivery limb may be cannulated with an arterial line of a cardiopulmonary bypass pump, such that blood is provided to parts of the body through the vascular device via the delivery limb during a procedure to position the vascular device. Alternatively or additionally, an endograft may be deployed via the delivery limb to engage the second end of the primary tubular structure.

In still other embodiments, a method for positioning a vascular device proximate a target site within a body lumen is provided in which a vascular device is provided including a first end, a second end, and a lumen extending therethrough, where at least one of the first or second ends comprises an inner skirt and an outer skirt that at least partially surrounds the outer skirt, and where the outer skirt is biased toward a rolled configuration such that an outer surface of the inner skirt is exposed. At least one of the first end or second end of the vascular device may be placed proximate a section of native blood vessel such that the outer surface of the inner skirt receives the section of native blood vessel. In addition, the outer skirt may be moved from the rolled configuration to an extended configuration, such that an inner surface of the outer skirt is disposed opposite the outer surface of the inner skirt, thereby engaging the section of native blood vessel therebetween.

In some cases, the inner skirt may be sutured to the respective section of native blood vessel prior to moving the outer skirt to the extended configuration. Additionally or alternatively, a length of the vascular device may be adjusted by trimming at least the inner skirt proximate at least one end of the vascular device. The outer skirt may be configured to promote hemostasis for minimizing endoleaks

BRIEF DESCRIPTION OF THE DRAWINGS

Figure 1:
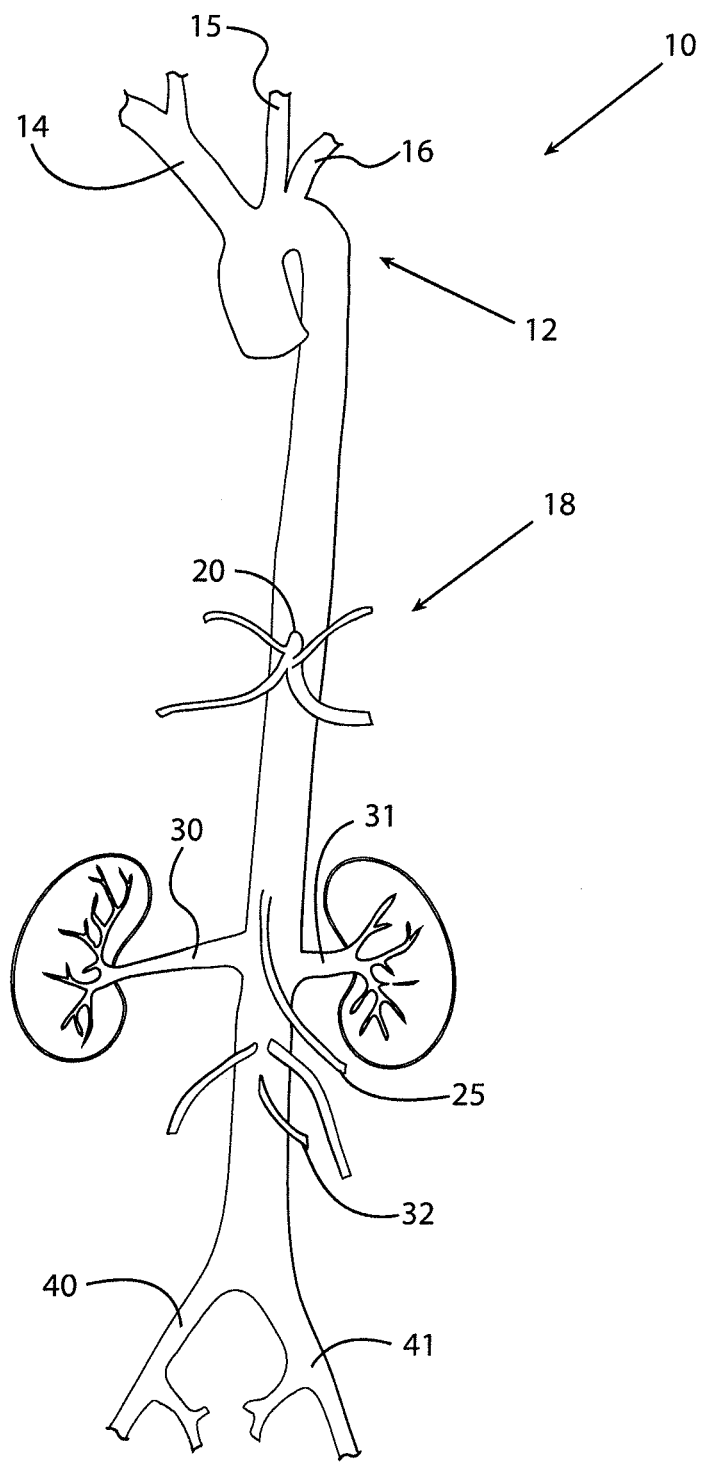
Figure 2:
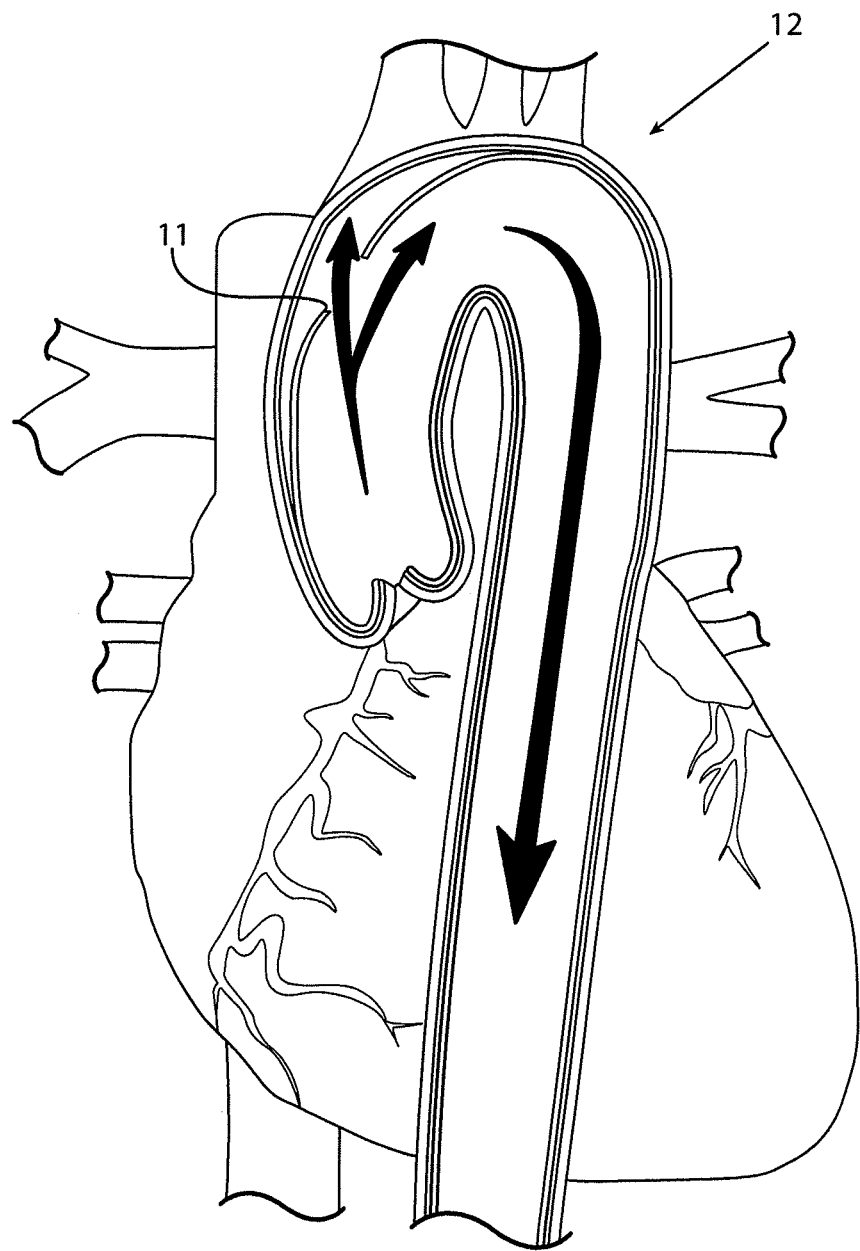
Figure 3:
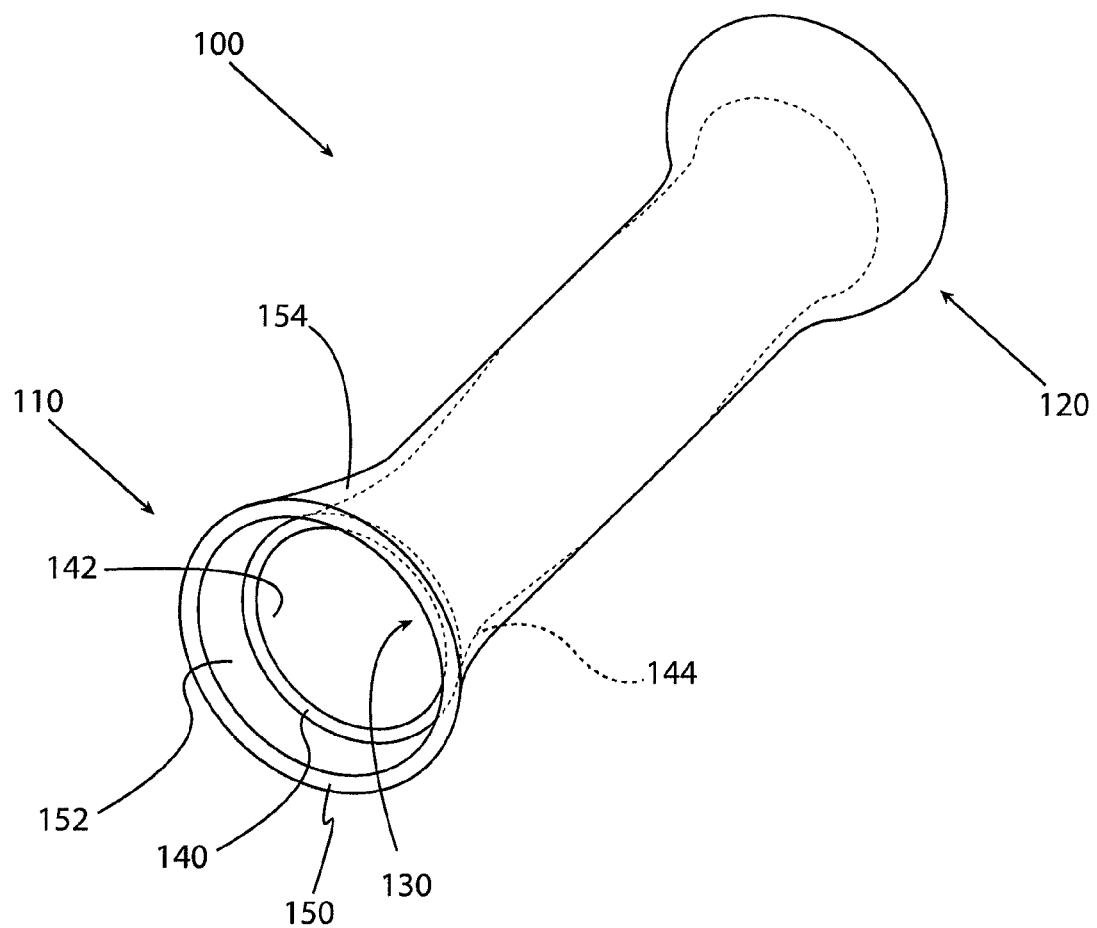
Figure 4A:
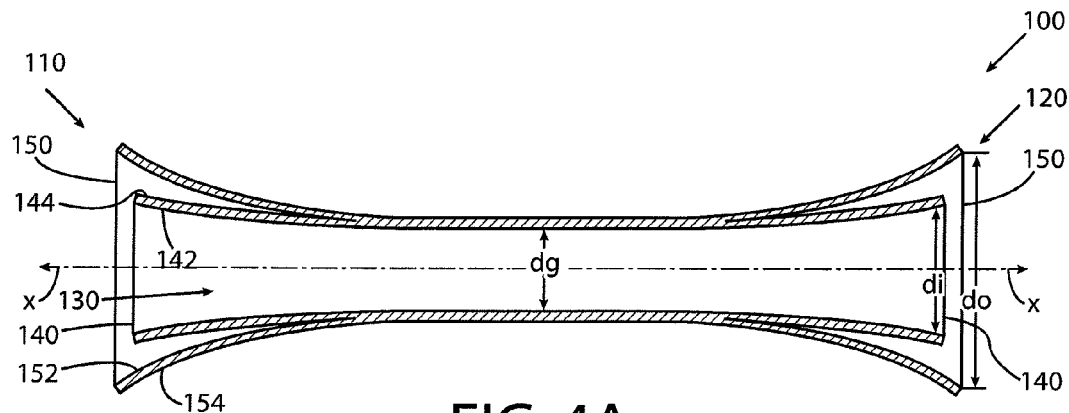
Figure 4B:
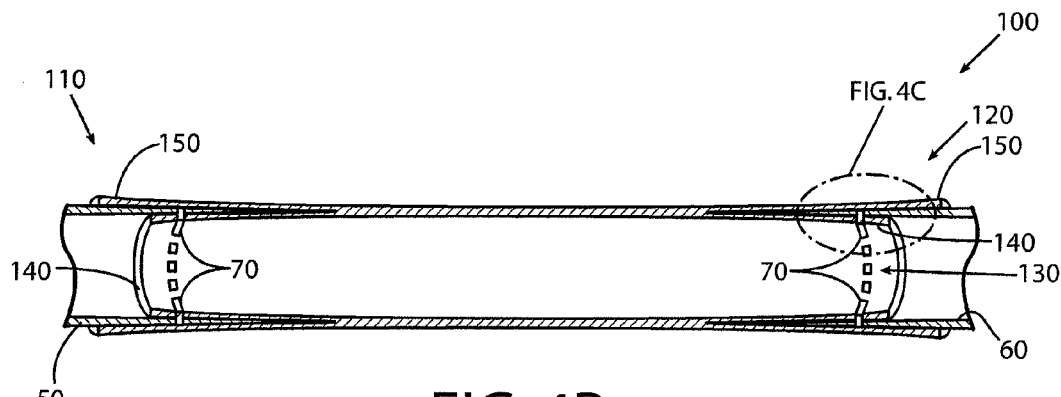
Figure 4C:
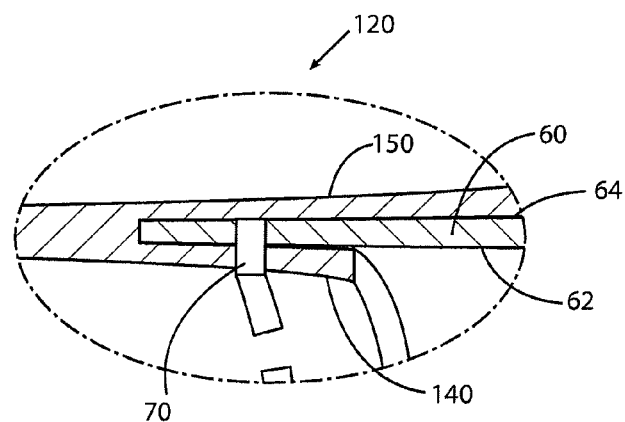
Figure 4D:
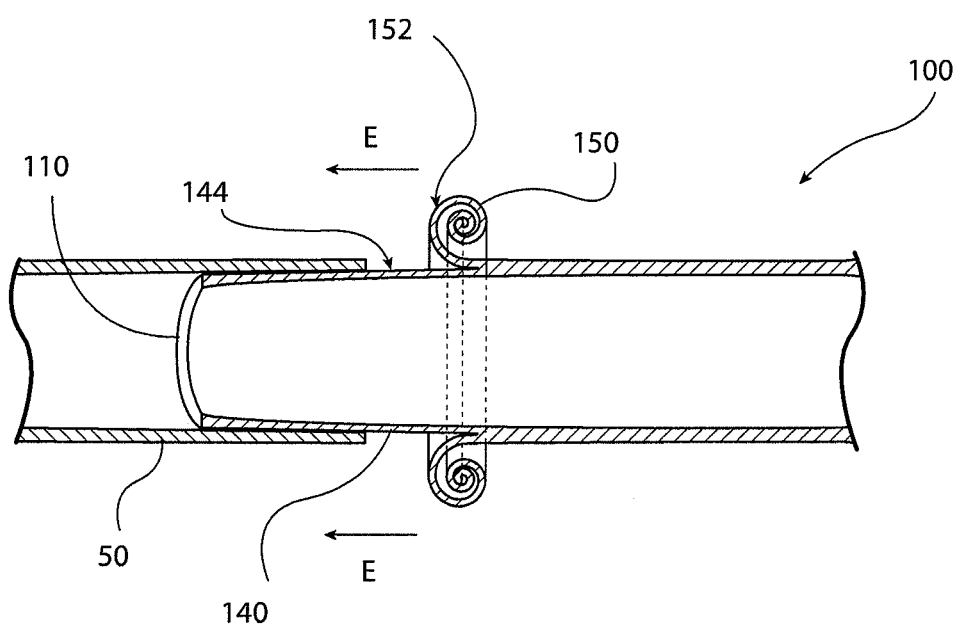
Figure 5:
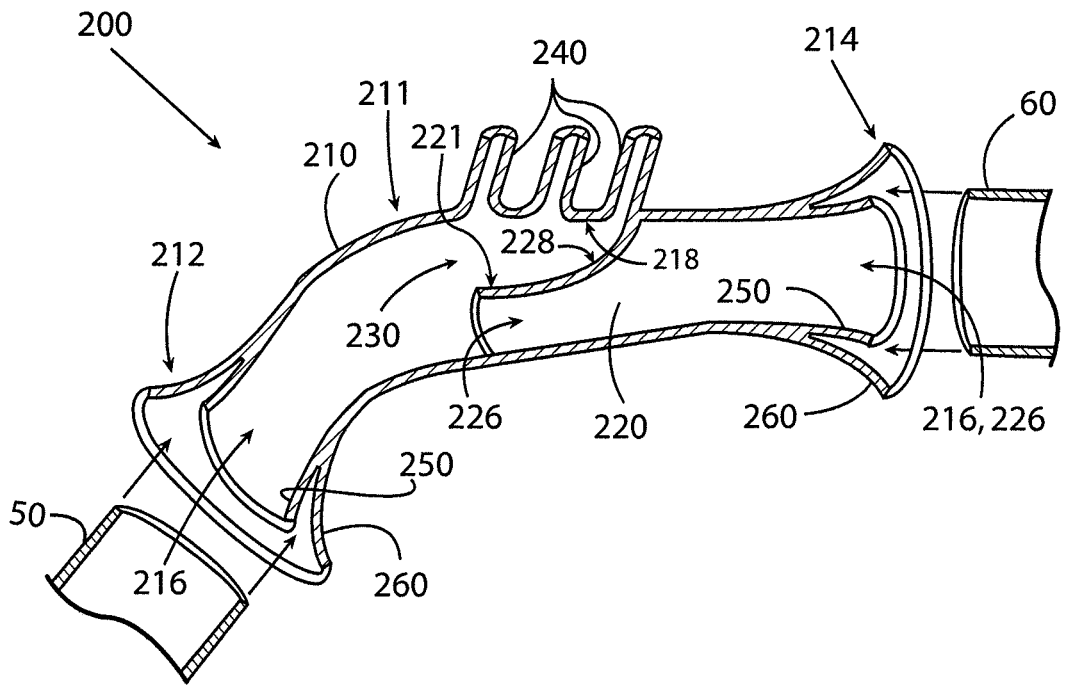
Figure 6:
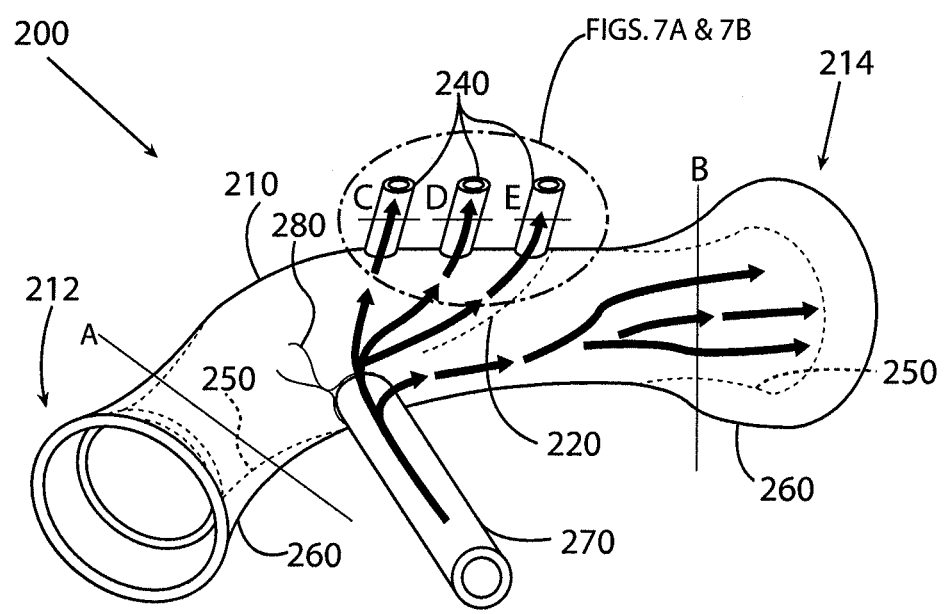
Figures 7A, 7B:
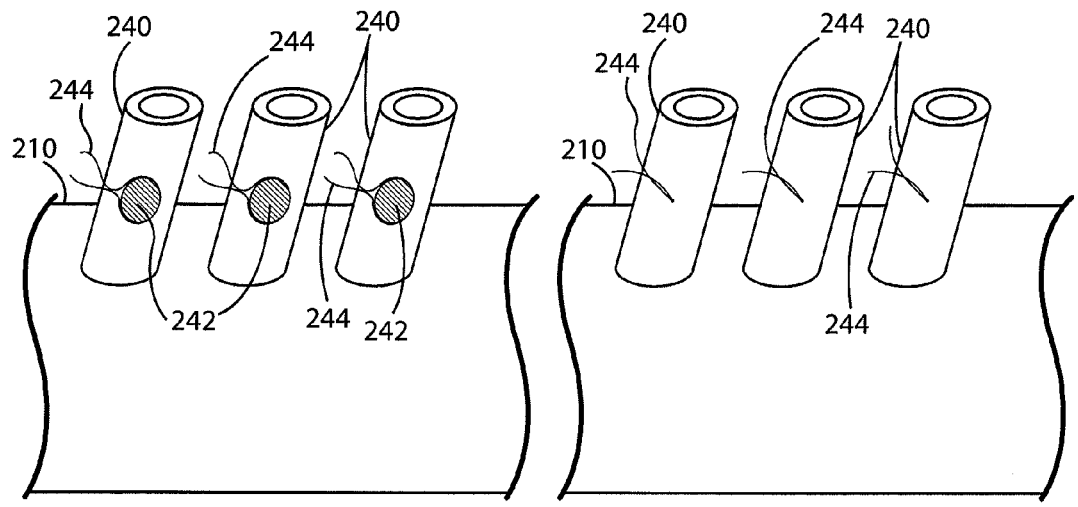
Figure 8:
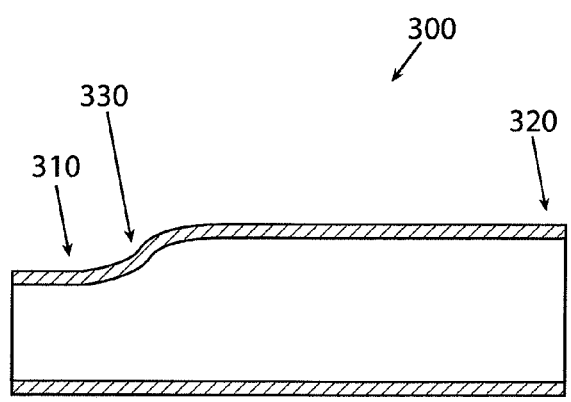
Figure 9:
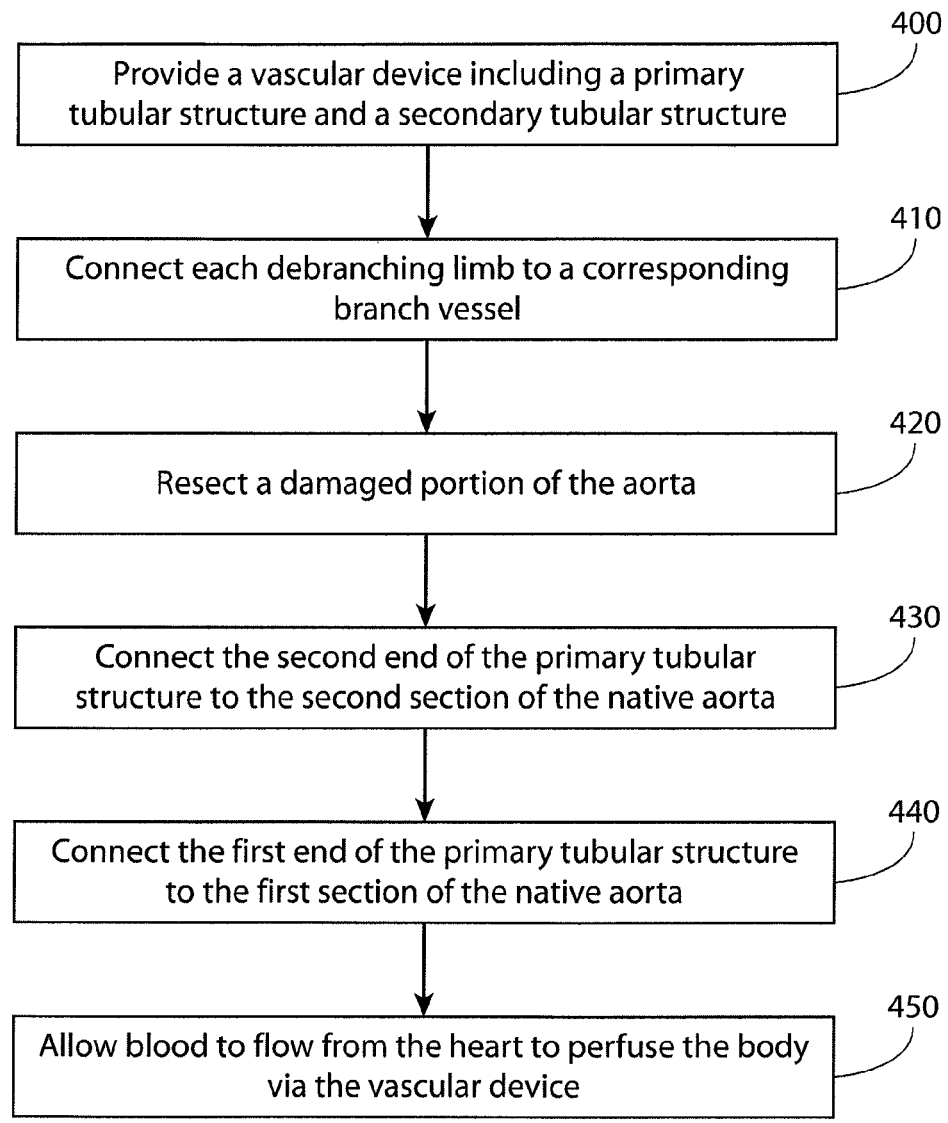

Having thus described the invention in general terms, reference will now be made to the accompanying drawings, which are not necessarily drawn to scale, and wherein:

FIG. 1 shows a schematic representation of an aorta with arterial branches;

FIG. 2 shows a schematic representation of a dissection in the aortic arch;

FIG. 3 shows a schematic perspective representation of a vascular device having inner and outer skirts in accordance with an exemplary embodiment of the present invention;

FIG. 4A shows a cross-sectional representation of the vascular device of FIG. 3 in accordance with an exemplary embodiment of the present invention;

FIG. 4B shows a cross-sectional representation of the vascular device of FIG. 4A engaged with respective sections of the native blood vessel in accordance with an exemplary embodiment of the present invention;

FIG. 4C shows a cross-sectional close up view of the engagement of a portion of the vascular device of FIG. 4A with the respective portion of the native blood vessel in accordance with an exemplary embodiment of the present invention;

FIG. 4D shows a cross-sectional representation of the vascular device in accordance with another exemplary embodiment of the present invention;

FIG. 5 illustrates a cross-sectional representation of a vascular device having debranching limbs and a secondary tubular structure in accordance with another exemplary embodiment of the present invention;

FIG. 6 illustrates a schematic perspective representation of the vascular device of FIG. 5 showing blood flow from an extracorporeal source after clamps at locations B, C, D, E, and F have been removed in accordance with an exemplary embodiment of the present invention;

FIG. 7A illustrates a schematic perspective representation of the debranching limbs of the vascular device of FIG. 6 before pursestrings are cinched in accordance with an exemplary embodiment of the present invention;

FIG. 7B illustrates a schematic perspective representation of the debranching limbs of the vascular device of FIG. 6 after the pursestrings are cinched in accordance with an exemplary embodiment of the present invention;

FIG. 8 illustrates a cross-sectional representation of an endograft configured to be received within the secondary tubular structure of the vascular device of FIG. 5 in accordance with another exemplary embodiment of the present invention; and FIG. 9 illustrates a flowchart of a method for positioning a vascular device proximate a target site within a body lumen in accordance with an exemplary embodiment of the present invention.

DETAILED DESCRIPTION

Some embodiments of the present invention will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, the terms "distal" and "distally" refer to a location farthest from a reference point, such as the heart; the terms "proximal" and "proximally" refer to a location closest to the reference point. Furthermore, although the examples described herein refer to a dissection in the aortic arch, embodiments of the described invention may be used to treat various vascular abnormalities requiring resection of a portion of the aorta, including aneurysms, type A dissections, and type B dissections, in various locations, including the ascending aorta, the aortic arch, the thoracic aorta, the abdominal aorta, and other blood vessels.

Thoracoabdominal aortic pathologies are often considered some of the most difficult aortic pathologies to treat. A schematic illustration of the aorta 10 is shown in FIG. 1. The ascending aorta and the aortic arch 12, for example, are sections that include a high degree of curvature, as well as arteries that branch up to feed oxygenated blood to the head, neck, and arms. Such arteries include the innominate artery 14, the left common carotid artery 15, and the left subclavian artery 16. The abdominal aorta 18, which begins at the diaphragm, also includes several important arterial branches that feed most of the major organs. Such arteries include the celiac artery 20, the superior mesenteric artery (SMA) 25, the renal arteries 30, 31, the inferior mesenteric artery (IMA) 32, and the femoral arteries 40, 41.

With reference to FIG. 2, aortic abnormalities, such as dissections 11, are some of the most serious conditions that can affect the aorta and often must be addressed immediately and effectively to minimize the patient's risk of death. In fact, it may be said that 50% of patients suffering from acute type A aortic dissections (i.e., dissections 11 involving the aortic arch 12, an example of which is shown in FIG. 2) are dead within 48 hours of the occurrence of the dissection.

Conditions such as dissections often require that the damaged section of the aorta be cut out and removed and that a prosthetic graft be sutured to the sections of native aorta that remain to take the place of the resected section. Conventional grafts typically require procedures involving deep hypothermic circulatory arrest (DHCA), in which the body of the patient is cooled to between 12° C. and 18° C. and blood circulation is stopped. The blood is drained from the body to eliminate blood pressure to allow the surgeon to remove the affected section of the aorta and install the graft in its place. As the patient is considered clinically dead during the operation, the duration of the operation becomes a major factor for determining the type and extent of negative consequences on the patient's health that may occur as a result of the surgery. For example, the risk of neurologic dysfunction following a period of DHCA is estimated at roughly 10% when the operation lasts less than 30 minutes, but increases to 15% at 40 minutes, 30% at 50 minutes, and 60% at 60 minutes. The complicated nature of such surgeries, and the possibility that the condition of the affected area may be worse than originally expected, often lengthen the anticipated duration of such procedures.

Such surgeries are even more difficult to perform when the dissection 11 occurs in sections of the aorta that include a number of arterial branches, such as in the aortic arch and the abdominal aorta, for example. With continued reference to FIGS. 1 and 2, blood flow must be maintained through the arterial branches themselves (such as the innominate artery 14, the left common carotid artery 15, and the left subclavian artery 16) during the surgery, which often requires the use of a graft having integral debranching limbs that can be extended through a portion of the native arterial branches. Often, the arterial branches themselves are in poor condition in the vicinity of the dissection, and suturing of the prosthetic graft and/or its debranching limbs to the native aorta and arterial branches thus creates a risk of endoleaks and tearing of the native vessels. Moreover, the anatomy of each patient is unique, creating variations in the size, spacing, and angle of the vessels. Conventional devices often fail to properly correspond to the particular patient's anatomy and, thus, the use of such devices may place stresses on the patient's vasculature, as well as on the device itself, due to improper sizing and/or differences between the angles at which the limbs join to the vascular device and the natural angles of the arterial branches with respect to the aortic arch.

Furthermore, in some cases, additional endografts may be required to address weaknesses or other abnormalities in the patient's vasculature, for example, downstream of the location of the graft. Conventional vascular devices, such as endografts and stents, require a section of vasculature proximal to and distal from the respective ends of the device to serve as "landing zones" to keep the endograft in position at the target site. For example, a landing zone of approximately 2 cm may be required. In the location of clusters of arterial branches, such as in the aortic arch 12, however, there is no 2 cm-section of aorta available to act as a landing zone due to the high density of arterial branches.

Accordingly, embodiments of the present invention provide for a vascular device and method for addressing aortic pathologies that is configured to facilitate hemostasis at the junctions of the ends of the device with the native aorta to minimize or eliminate the risk of endoleaks. In addition, embodiments of the present invention provide for a vascular device and method for addressing aortic pathologies that are configured to allow the device to be installed in the patient's vasculature without the need for DHCA, minimizing the risks to the patient associated with the repair procedure. Moreover, embodiments of the vascular device and method may facilitate use of the graft with other devices and other procedures, such as in cases in which stent-grafts are needed in the aorta near the area of graft and/or in the nearby arterial branches.

With reference to FIGS. 3 and 4A-4D, embodiments of the vascular device 100 for treating a target site within a body lumen are provided, where the vascular device is configured for placement between first and second sections 50, 60 of the patient's native blood vessel (the aorta in the depicted example of FIGS. 4B, 4C, and 4D). Embodiments of the vascular device 100 comprise a first end 110 configured to be attached to the first section 50 of the native blood vessel and a second end 120 configured to be attached to the second section 60 of the native blood vessel. The vascular device 100 may be generally tubular, as shown in FIG. 3, and may define a lumen 130 extending between the first and second ends 110, 120.

At least one of the first or second ends 110, 120 may comprise an inner skirt 140 and an outer skirt 150, and the inner and outer skirts may be configured to receive a portion of the respective section 50, 60 of the patient's native blood vessel therebetween for attaching the respective end of the vascular device 100 to the respective section of the native blood vessel, as shown in FIGS. 4B and 4C and described in greater detail below. In some embodiments, such as the depicted embodiment of the figures, each end 110, 120 of the vascular device 100 may comprise an inner skirt 140 and an outer skirt 150 that at least partially surrounds the inner skirt. The vascular device 100 may be configured to receive a portion of the respective section of the native blood vessel between the inner and outer skirts 140, 150 for attaching the respective end of the vascular device to the respective section 50, 60 of the native blood vessel. In other embodiments, however, an inner and outer skirt 140, 150 may only be provided on one of the two ends 110, 120, as needed.

Each of the inner skirt 140 and the outer skirt 150 may have a tubular configuration, as illustrated in FIG. 3, and may extend away from a central axis X defined by the vascular device 100, thereby forming a flare as shown in FIG. 4A. As a result of the flare, the diameter di of the vascular device 100 at the end of the inner skirt 140 may be greater than the diameter dg of the main body of the graft, as illustrated in FIG. 4A. The outer skirt 150 may form a larger flare than the inner skirt 140, and as such the diameter do of the vascular device 100 measured between opposite points on the outer skirt at a location corresponding to the location of the diameter di of the inner skirt 140 may be larger than the diameter di of the inner skirt. In other cases, however, the degree of flaring on the inner and outer skirts 140, 150 may be approximately the same. For example, in some embodiments, the diameter dg of the main body of the graft may be approximately between 20 mm and 40 mm; the diameter di of the vascular device 100 at the end of the inner skirt 140 may be approximately between 25 mm and 60 mm; and the diameter do of the vascular device 100 measured between opposite points on the outer skirt may be approximately between 30 mm and 60 mm.

Providing inner and outer skirts 140, 150 that include flares may allow for a "one-size-fits-all" vascular device, or at least minimize the number of different sizes of devices that need to be made available to accommodate patients with different anatomies. In this regard, the physician may be able to customize the vascular device 100 to fit a particular patient's anatomy by trimming one or both ends 110, 120 of the device to effectively reduce the diameter di of the inner skirt at the respective end 110, 120 of the device to match the diameter of the respective section 50, 60 of the native blood vessel to which it will be attached. For example, in a patient with a relatively larger diameter aorta, a very small portion of the respective ends 110, 120 of the device 100 may be trimmed (or not at all) to allow the diameter of the device to correspond to the diameter of the native aorta, whereas in a patient with a relative smaller diameter aorta, a larger portion of the respective ends of the device may be trimmed to fit the device.

With continued reference to FIG. 4A, the inner skirt 140 may define an inner surface 142 extending circumferentially about the lumen 130 and an outer surface 144 disposed on an opposite side of the inner skirt. Similarly, the outer skirt 150 may define an inner surface 152 disposed closest to the inner skirt 140 and an outer surface 154 disposed on an opposite side of the outer skirt. As illustrated in FIGS. 4B and 4C, the vascular device 100 may be configured such that the outer surface 144 of the inner skirt 140 is configured to be disposed adjacent the inner surface 62 of the respective section of the native blood vessel 60 and the inner surface 152 of the outer skirt 150 is configured to be disposed adjacent the outer surface 64 of the respective section of the native blood vessel. Said differently, the end of the respective section 60 of the native blood vessel may be received between opposing surfaces 144, 152 of the inner and outer skirts 140, 150.

Accordingly, in some embodiments, the inner skirt 140 may be configured to be sutured to the respective section 50, 60 of the native blood vessel, for example, via sutures 70 shown in FIGS. 4B and 4C. The outer skirt 150 may, in turn, be configured to promote hemostasis of the suture line 70 for minimizing endoleaks proximate the respective end, for example, as a result of the outer skirt 150 resting against the line of sutures 70 once the vascular device is in place. For example, blood leaking through holes in the material of the inner skirt 140 and the corresponding section 60 of the aorta resulting from the suture 70 (e.g., where the suture passes between the two materials to hold them together) may seep between the outer surface 64 of the aorta and the inner surface 152 (shown in FIG. 4A) of the outer skirt 150. Due to the presence of the outer skirt 150 against these holes, however, any such blood seepage is slowed down, and eventually blood that has seeped between the aortic wall 60 and the outer skirt 150 clots and, in turn, serves to further plug the holes against any additional leakage. In other words, the outer skirt 150 facilitates the clotting of blood in the area between the aorta and the outer skirt and, in essence, seals the line of suture against endoleaks. Thus, in some embodiments, the outer skirt 150 may be configured to have a longer length than the inner skirt 140, so as to provide additional surface area over which such clotting may form. In other cases, the outer skirt 150 may be biased inwardly (e.g., toward the central axis X) or may exert a clamping force (by itself or when used in conjunction with a separate tie or lasso disposed circumferentially on an exterior of the outer skirt). Accordingly, although in FIG. 4A the inner and outer skirts 140, 150 are shown having a separation therebetween prior to engagement with the native aorta for explanatory purposes, the inner and outer skirts may be disposed against each other (with no separation) prior to engagement so as to exert such bias or clamping force along the line of suture in some embodiments once in place.

In some embodiments, for example, the outer skirt 150 may be configured to be moved between a first position and a second position. With reference to FIG. 4D, which shows the first position, the outer skirt 150 may be biased toward a rolled configuration, such that the outer surface 144 of the inner skirt 140 is exposed for receiving the respective section of native blood vessel 50 (e.g., the section of the aorta) thereon, as shown. In other words, prior to installation of the device 100 at the target site, in the first position, the outer skirt 140 may have a rolled configuration, and as a result the inner surface 152 of the outer skirt may be displaced from the outer surface 144 of the inner skirt 140.

Once the section of native blood vessel 50 has been adequately engaged with the outer surface 144 of the inner skirt 140, the outer skirt 150 may be rolled out (e.g., in the direction E shown in FIG. 4D) by the surgeon from the first position of FIG. 4D to the second position, in which the outer skirt is biased toward an extended configuration (e.g., as shown in FIG. 4B), such that the inner surface 152 of the outer skirt is disposed opposite the outer surface 144 of the inner skirt 140. In this way, the respective section of native blood vessel 50 may be engaged between the inner and outer skirts 140, 150, as described above. Moreover, in some embodiments, in the second position (FIG. 4B), the outer skirt 150 may be configured to apply pressure in a direction toward the inner skirt 140, so as to promote hemostasis for minimizing endoleaks, as well as to resist returning to the first position (FIG. 4D).

For example, the surgeon may position the vascular device 100 at the target site, placing at least one of the first or second ends 110, 120 having the inner and outer skirts 140, 150 proximate the respective section of native blood vessel 50, 60 such that the outer surface 144 of the inner skirt 140 receives the section of native blood vessel thereon. The surgeon may, in some cases, suture the inner skirt 140 to the respective section of native blood vessel 50, 60 while the outer skirt 150 is in the first position of FIG. 4D, then may move the outer skirt from the rolled configuration of FIG. 4D to the extended configuration of FIG. 4B, such that the inner surface 152 of the outer skirt 150 is disposed opposite the outer surface 144 of the inner skirt 140. In this way, the respective section 50, 60 of native blood vessel may be engaged between the inner and outer skirts 140, 150. As noted above, depending on the length of the resected portion of the blood vessel, the surgeon may initially need to adjust a length of the vascular device 100 by trimming at least the inner skirt 140 proximate the end of the vascular device having the inner and outer skirts 140, 150, such that the vascular device will properly accommodate the respective section of native blood vessel 50, 60.

The vascular device 100, including the inner and outer skirts 140, 150, may be made of a polymer material, such as polyester, Dacron® material, polytetrafluoroethylene (PTFE), and/or Gore-tex® fabric. The polymer material may, in some cases, be structurally reinforced via a metal mesh, such as via stainless steel, nitinol, or other biocompatible metal. The outer skirt 150 may be formed integrally with the vascular device 100 and the inner skirt 140 or, in some embodiments, may be a separate structure that is attached to the material of the vascular device, such as via fasteners (e.g., stitching of the respective materials together), adhesive, bonding, or other type of connection.

In some cases, depending on the condition of the patient and the extent of vascular damage, resection of a portion of the aorta and replacement of the resected section with a vascular device such as the device 100 described above may not be enough to address all of the pathologies present. For example, portions of the native vessel downstream of the resected section, although not themselves requiring resection, may be weakened and may need to be supported to prevent future complications due to aneurysms or additional dissections. Accordingly, upon installing the vascular device, it may be necessary for the surgeon to introduce an additional stent-graft intravascularly (e.g., through at least a portion of the lumen 130 of the vascular device 100) to support the weakened sections of the aorta and/or arterial branches located proximate the target site where the device 100 was installed. Thus, the vascular device 100 may be configured in some cases such that at least one of the first or second ends 110, 120 of the vascular device is configured to receive an endograft. In areas of the vasculature including clusters of arterial branches, introduction of an endograft poses the challenge of maintaining the arterial branches open to allow adequate blood flow to the respective body parts, as well as providing a sufficient landing zone to allow the endograft to be securely connected to the vascular device so as to minimize the risk of migration of the endograft over time.

Turning to FIG. 5, for example, one embodiment of a vascular device 200 is depicted that includes a primary tubular structure 210 comprising a first end 212, a second end 214, and a primary lumen 216 extending between the first and second ends. A secondary tubular structure 220 may be disposed within the primary lumen 216 of the primary tubular structure 210, and the secondary tubular structure may comprise a secondary lumen 226. The secondary tubular structure 220 may be configured to receive an endograft 300 (shown in FIG. 8) via the secondary lumen 226 and may be configured to serve as a landing zone for the endograft, as described in greater detail below.

Accordingly, in some embodiments, at least a portion of the outer surface 228 of the secondary tubular structure 220 may be spaced from a corresponding inner surface 218 of the primary tubular structure 210, thus defining a chamber 230 therebetween. In some cases, a portion of the secondary tubular structure 220 coincides with a portion of the primary tubular structure 210, as shown in FIG. 5. In other words, a portion of the secondary tubular structure 220 may be integral to the primary tubular structure 210, such that the two structures effectively share the same wall in the area of overlap, as depicted. Accordingly, due to the generally tubular configurations of the primary and secondary tubular structures 210, 220, the chamber 230 may be configured to have a crescent moon shaped cross-section.

For example, the primary tubular structure 210 may be made of a polymer material, such as polyester, Dacron® material, polytetrafluoroethylene (PTFE), and/or Gore-tex® fabric. The polymer material of the primary tubular structure 210 may, in some cases, be structurally reinforced via a metal mesh, such as via stainless steel, nitinol, or other biocompatible metal. The secondary tubular structure 220 may be made of a metal mesh (e.g., stainless steel, nitinol, or other biocompatible metal) that is surrounded by a polymer fabric, such as Gore-tex®. Thus, in embodiments in which a portion of the secondary tubular structure 220 is integral to the primary tubular structure 210, as depicted, the metal mesh of the secondary tubular structure may be embedded into the same polymer material that forms the primary tubular structure.

With continued reference to FIG. 5, the vascular device 200 may further comprise one or more debranching limbs 240 extending from the primary tubular structure 210 in the area of the chamber 230. Each debranching limb 240 may correspond to a branch vessel such that blood is able to flow through each debranching limb via the chamber 230 to the corresponding branch vessel. For example, each debranching limb 240 may be substantially aligned with a branch vessel such that the surgeon may be able to attach (e.g., via sutures) each limb with its corresponding branch vessel, as described in greater detail below. In the embodiment depicted in FIG. 5, for example, three debranching limbs 240 are provided, with each limb corresponding to one of the innominate artery 14, the left common carotid artery 15, and the left subclavian artery 16 (shown in FIG. 1), respectively. In other cases, however, only one or two debranching limbs 240 may be provided, depending on the number of branch vessels that need to be attached and/or the particular procedure to be performed. Moreover, although not shown in the depicted embodiment, in some embodiments, the end of one or more of the debranching limbs 240 may be configured to include inner and outer skirts such that the outer skirt wraps around the suture line between the respective debranching limb and the corresponding arterial branch, similar to the descriptions above with respect to FIGS. 3-4D.

Furthermore, blood may be able to flow through the secondary lumen 226 defined by the secondary tubular structure 220 to points downstream, including the descending aorta and its branch vessels in the depicted embodiment. In this regard, in some embodiments, the primary tubular structure 210 may be configured such that an expanded volume portion, or bulge 211, is provided proximate an interior end 221 of the secondary tubular structure 220. The bulge 211 may be configured such that approximately half of the blood flow through the first end 212 of the primary tubular structure 210 is directed to the chamber 230 and the one or more debranching limbs 240 and the other half of the blood flow is directed into the secondary tubular structure 220 for perfusion of downstream vessels and organs. Said differently, the secondary tubular structure 220 may act as a flow divider, and the bulge 211 may facilitate the adequate distribution of blood through the vascular device 200.

In some embodiments, the vascular device 200 may be configured such that the inner diameter of the device proximate first end 212 is approximately between 36 mm and 46 mm (e.g., with various sizes available in increments of 2 mm). The inner diameter of the secondary tubular structure 220 proximate the interior end 221 may, in turn, be approximately between 20 mm and 36 mm (e.g., with various sizes available in increments of 2 mm). Accordingly, the inner diameter of the primary tubular structure 210 proximate the interior end 221 of the secondary tubular structure 220 (e.g., between two opposite points of the primary tubular structure in the vicinity of the bulge 211) may be between 40 mm and 72 mm, respectively.

The vascular device 200 may, in some cases, such as in the depicted embodiment, be configured such that at least one of the first or second ends 212, 214 of the primary tubular structure includes an inner skirt 250 and an outer skirt 260. In the depicted embodiment, both ends 212, 214 comprise inner and outer skirts 250, 260. The inner and outer skirts 250, 260 may be configured similarly to the inner and outer skirts 140, 150 illustrated in FIGS. 3-4D and the associated description provided above for facilitating hemostasis at the ends of the device 200 where the device is joined to sections of the native aorta 50, 60. In such embodiments, the inner skirt 250 and the outer skirt 260 may be configured to receive a portion of a respective section of a native blood vessel therebetween for attaching the respective end 212, 214 of the primary tubular structure 210 to the respective section 50, 60 of the native blood vessel, as described above.

Turning now to FIG. 6, embodiments of the vascular device 200 may be placed at the target site and attached to the respective blood vessels and branch vessels to treat a vascular abnormality, such as a Type A dissection, without requiring the use of DHCA. One example of a method for treating a vascular abnormality using an embodiment of the vascular device 200 is provided below, although different variations of the described method may be used depending on the anatomy and condition of the patient, the particular vascular pathology being treated, and the surgeon's preferences.

In some embodiments, for example, a cardiopulmonary bypass may be used to allow the surgeon to resect the damaged portion of the aorta, connect the vascular device 200 to the native blood vessels, and restore anatomic blood flow. In such a procedure, two clamps are initially applied to the vascular device 200 at locations A and B shown in FIG. 6, with smaller clamps being applied to each debranching limb 240 at C, D, and E. Upon gaining access to the target site (e.g., via a thoracotomy), the heart is stopped and blood and oxygen are circulated through the body via an extracorporeal pump (e.g., a cardiopulmonary bypass pump).

In this regard, embodiments of the vascular device 200 may comprise a delivery limb 270 extending from the primary tubular structure 210, proximate the first end 212, but between the locations A and B where the clamps are applied to the device. The delivery limb 270 may be integral to the vascular device 200 and may comprise a metal mesh (e.g., stainless steel, nitinol, or other biocompatible metal) surrounded by Gore-tex® fabric. In some embodiments, the delivery limb 270 may have a diameter of between approximately 12-20 mm, such as, for example, 16 mm. The delivery limb 270 may be cannulated with the arterial line of the cardiopulmonary bypass pump, and the air may be withdrawn from the volume of the device 200 formed by application of the clamps at locations A, B, C, D, and E. The innominate artery of the patient may then be transected, and the corresponding debranching limb 240 may be attached to the native arterial branch via suturing or an endovascular technique (described below).

At this point, the respective clamp (e.g., at location C) may be removed, and the cardiopulmonary bypass pump may be started. The left carotid artery may then be transected and attached to the corresponding debranching limb 240, whereupon the corresponding clamp (e.g., at location D) may be removed and blood may be allowed to flow through the vascular device 200 and the respective debranching limb 240. Similarly, the left subclavian artery may be transected and attached to the corresponding debranching limb 240, and blood from the cardiopulmonary bypass pump may be allowed to flow to the left subclavian artery via the corresponding debranching limb (e.g., by removing the clamp at location E). In some cases, the arterial line of the cardiopulmonary bypass pump may be branched such that one line goes to the delivery limb 270, while another line can be used to supply blood to the lower body, such as via femoral access or temporary left subclavian artery access.

Once the upper body is being perfused via the cardiopulmonary bypass pump, (and, for example, the lower body is being perfused via the second arterial line from the pump mentioned above), the heart may be stopped, the native aortic arch may be clamped, and the damaged section of the aorta may be removed (not shown). The inner skirt 250 at the second end 214 of the primary tubular structure 210 may then be sutured to the respective end of the native aorta 60 (illustrated in FIG. 5), and the clamps on both the aortic arch (not shown) and the vascular device 200 (at location B) may be removed. At this point, the cardiopulmonary bypass pump may be used to perfuse to the entire body via the vascular device 200, as illustrated via arrows in FIG. 6.

In addition to providing arterial access for the cardiopulmonary bypass pump, the delivery limb 270, may be used to deploy an endograft 300 (shown in FIG. 8) that is configured to engage the second end 214 of the primary tubular structure 210 via the landing zone provided by the secondary tubular structure 220, if necessary to address vascular abnormalities distal to the vascular device 200. With reference to FIG. 8, the endograft 300 may comprise a polymer fabric, such as Gore-tex® fabric, that is supported by a metal mesh, as described above with respect to the debranching limbs 240.

The endograft 300 may be delivered through the delivery limb 270, a portion of the primary tubular structure 210, and the secondary tubular structure 220 in a collapsed state, such as through a delivery catheter. The endograft 300 may further be configured to include a narrow diameter portion 310, a larger diameter portion 320, and a tapered portion 330 extending therebetween on at least one side (e.g., covering 180°) of the endograft. The tapered portion 320 may, in some embodiments, extend between a substantially cylindrical narrow diameter portion 310 and a substantially cylindrical larger diameter portion 320. In other embodiments, the tapered portion 320 may extend from the narrow diameter end of the endograft to the larger diameter portion, giving the endograft 300 a conical configuration on one end that substantially corresponds to the shape of the secondary tubular structure 220. The endograft 300 may be configured to assume the tapered configuration upon its expansion (e.g., via self-expansion of a shape memory alloy, such as nitinol, or via balloon expansion or other expansion mechanisms) such that the endograft securely engages the secondary tubular structure 220. Accordingly, in some embodiments, the endograft 300 may be selected such that it is approximately 2 to 4 mm larger in diameter than the diameter of the secondary tubular structure 220 (so as to provide a more secure fit with the secondary tubular structure upon its expansion).

At this point, the first end 212 of the primary tubular structure 210 may be attached to the heart or a respective end of the native aorta 50 close to the heart, and the clamp at location A may be removed. Additional procedures to the heart may be performed, if necessary, such as valve replacement bypass surgery. Once any additional procedures necessary have been completed, the patient may be gradually weaned off the cardiopulmonary bypass pump, and natural blood flow from the heart (via the vascular device 200) may be resumed.

After the procedure is complete and the delivery limb 270 is no longer needed, the delivery limb may be cut by the surgeon proximate the surface of the primary tubular structure 210. In this regard, in some embodiments, the junction of the delivery limb 270 with the primary tubular structure 210 may comprise a built-in suturing mechanism in the form of pursestrings 280 that can be pulled by the surgeon to close off the opening in the primary tubular structure corresponding to the delivery limb. Thus, once the delivery limb 270 is trimmed and the pursestrings 280 have been pulled, the material of the primary tubular structure may be cinched together to close off the opening and prevent blood from flowing out of the vascular device 200 through that opening. The pursestrings 280 may, for example, be made of Gore-tex® material in some cases.

Similarly, with reference to FIG. 7A, one or more of the debranching limbs 240 may include a weakened region 242 (e.g., a "soft spot") where the surgeon may insert a needle to introduce a guidewire and deliver additional endografts into the respective arterial branches, if needed. An endograft may be needed, for example, in cases where suturing the native branch vessel to the debranching limb 240 may be risky or technically difficult to accomplish, for example, due to weak or damaged areas of the branch vessel.

Each weakened region 242 may be surrounded by a pursestring 244 that is configured to be pulled by the surgeon to close off any holes made by the surgeon in delivering an endograft via the weakened region 242. An embodiment in which the pursestrings 244 have been pulled closed is shown in FIG. 7B. Each pursestring 244 may be provided at the interface between the standard material of the debranching limb 240 and the material making up the weakened region 242, such that once the pursestrings 244 are cinched closed, substantially all of the debranching limb 240 would be comprised of the standard material (e.g., the material forming the weakened region 242 would account for little to none of the material of the overall debranching limb).

The weakened region 242 may be made of a different material than the rest of the debranching limb such that it is easier for a surgeon to puncture, or the region 242 may be made of the same material as the rest of the debranching limb 240, but may be a region of reduced thickness. As noted above, the pursestrings 244 may be made of Gore-tex® fabric. Furthermore, an additional layer of Gore-tex® fabric may be provided on top the pursestrings 244 to enhance the structural integrity of the interface between the debranching limb 240 and the weakened region 242.

A method for positioning a vascular device proximate a target site within a body lumen as described above is summarized in FIG. 9. The method includes providing a vascular device at Block 400. For example, the vascular device in some embodiments may be configured similarly to the vascular device 200 shown in FIGS. 5-7B and may include a primary tubular structure comprising a first end, a second end, and a primary lumen extending between the first and second ends. The device may further include a secondary tubular structure disposed within the primary lumen of the primary tubular structure and comprising a secondary lumen, where at least a portion of an outer surface of the secondary tubular structure is spaced from an inner surface of the primary tubular structure and defines a chamber therebetween. In addition, at least one debranching limb may extend from a portion of the primary tubular structure in the area of the chamber.

Each debranching limb may be connected to a corresponding branch vessel such that blood is able to flow through each debranching limb via the chamber to the corresponding branch vessel at Block 410, such as using a procedure involving a cardiopulmonary bypass, as described above. A damaged portion of the aorta may be resected, such that a first section and a second section of the native aorta remain in the body lumen at Block 420. In some cases, where the dissection is very close to the heart, the first section of the native aorta may actually be part of the heart.

The second end of the primary tubular structure may be connected to the second section of the native aorta such that blood is able to flow through the secondary lumen to points downstream at Block 430, and the first end of the primary tubular structure may be connected to the first section of the native aorta at Block 440. In cases where a cardiopulmonary bypass pump was used to perfuse the body during the procedure, as described above, the patient may be weaned off the pump and blood may be allowed to flow from the heart to perfuse the body via the vascular device at Block 450.

Although the description herein uses the example of a device that is configured for treatment of a target site in the aortic arch (e.g., in the area of the innominate artery, the left common carotid artery, and the left subclavian artery), conditions in other areas of the aorta may also be addressed using embodiments of the vascular device. For example, different configurations of the vascular device 200 may be provided to address pathologies of the visceral aorta in the area of the celiac artery, SMA, and renal arteries. In areas of the vasculature that are not near clusters of arterial branches, embodiments of the vascular device 100 shown in FIGS. 3-4D and described may be used.

Embodiments of the vascular device described above may provide several advantages for the treatment of vascular abnormalities such as aneurysms and dissections, including abnormalities in areas of the patient's vasculature near clusters of branch vessels. For example, embodiments of the device may be provided that are configured to fit a greater patient population without the need for multiple sizes of devices, such as when inner and outer skirts are provided that can be customized at the time of the procedure to accommodate the particular patient's anatomy. Moreover, embodiments of the device may be used for various locations of the vasculature, including in the aortic arch and the thoracoabdominal aorta.

Notably, embodiments of the vascular device may allow the surgeon to perform a total aortic arch replacement without the need for deep hypothermic circulatory arrest (DHCA), which reduces the risks of patient morbidity and mortality that are commonly associated with this type of procedure. Moreover, the use of shape memory alloys such as nitinol in such devices may be facilitated, as the patient's body temperature no longer needs to be reduced for purposes of the DHCA, which typically affects the self-expansion of such metals. In addition, bleeding at the interface between the device and the native vessels (e.g., where the device is sutured to the native vessels) may be significantly reduced, as described above, allowing for a more hemostatic aortic replacement.

The design of embodiments of the vascular device including primary and secondary tubular structures, as described above, may further allow the vascular device to have a more compact configuration that is easier to fit in the patient's mediastinum. The configuration of the vascular device, in some embodiments, may also assist in securing an endograft to the end of the device, e.g., by providing a landing zone within the vascular device, and may minimize the occurrence of endoleaks.

The devices and methods depicted in the figures and described above represent only certain configurations of the vascular device and method of delivering the device. The particular configurations and methods of delivery will depend on the patient's anatomy, the condition and location of the target site, the preferences of the practitioner, and other considerations.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A vascular device for treating a target site within a body lumen, wherein the vascular device is configured for placement between first and second sections of a patient's native blood vessel, the vascular device comprising:
   a first end configured to be attached to the first section of the native blood vessel;
   a second end configured to be attached to the second section of the native blood vessel; and
   a lumen extending between the first and second ends, wherein the lumen is defined by a wall,
   wherein the wall splits proximate at least one of the first or second ends to form an inner skirt and an outer skirt, wherein the outer skirt at least partially surrounds the inner skirt, and wherein the inner and outer skirts are spaced from each other and are thereby configured to receive a portion of the respective section of the native blood vessel within the space formed between the inner and outer skirts for attaching the respective end of the vascular device to the respective section of the native blood vessel,
   wherein the inner skirt is configured to be attached to the respective section of the native blood vessel and the outer skirt is configured to be placed against an outer surface of the attachment between the inner skirt and the respective section of the native blood vessel, such that the respective section of the native blood vessel is disposed between the inner skirt and the outer skirt, and
   wherein the outer skirt is longer than the inner skirt.

2. The vascular device of claim 1, wherein an outer surface of the inner skirt is configured to be disposed adjacent an inner surface of the respective section of the native blood vessel and an inner surface of the outer skirt is configured to be disposed adjacent an outer surface of the respective section of the native blood vessel.

3. The vascular device of claim 1, wherein each end of the vascular device comprises an inner skirt and an outer skirt configured to receive a portion of the respective section of the native blood vessel therebetween for attaching the respective end of the vascular device to the respective section of the native blood vessel.

4. The vascular device of claim 1, wherein the inner skirt is configured to be sutured to the respective section of the native blood vessel and the outer skirt is configured to promote hemostasis for minimizing endoleaks proximate the respective end.

5. The vascular device of claim 1, wherein each of the inner and outer skirts extends away from a central axis defined by the vascular device, thereby forming a flare.

6. The vascular device of claim 1, wherein the outer skirt is configured to be moved between a first position and a second position, wherein in the first position the outer skirt is biased toward a rolled configuration, such that an outer surface of the inner skirt is exposed for receiving the respective section of native blood vessel, and in the second position the outer skirt is biased toward an extended configuration, such that an inner surface of the outer skirt is disposed opposite the outer surface of the inner skirt, thereby engaging the respective section of native blood vessel therebetween.

7. The vascular device of claim 6, wherein in the second position the outer skirt is configured to apply pressure in a direction toward the inner skirt.

8. A vascular device for treating a target site within a body lumen, wherein the vascular device is configured for placement between first and second sections of a patient's native blood vessel, the vascular device comprising:
   a first end configured to be attached to the first section of the native blood vessel;
   a second end configured to be attached to the second section of the native blood vessel; and
   a lumen extending between the first and second ends, wherein the lumen is defined by a wall,
   wherein the wall splits proximate at least one of the first or second ends to form an inner skirt and an outer skirt, wherein the outer skirt at least partially surrounds the inner skirt, and wherein the inner and outer skirts are spaced from each other and are thereby configured to receive a portion of the respective section of the native blood vessel within the space formed between the inner and outer skirts for attaching the respective end of the vascular device to the respective section of the native blood vessel,
   wherein the inner skirt is configured to be attached to the respective section of the native blood vessel and the outer skirt is configured to be placed against an outer surface of the attachment between the inner skirt and the respective section of the native blood vessel, such that the respective section of the native blood vessel is disposed between the inner skirt and the outer skirt, and
   wherein one of the first or second ends is configured to receive an endograft therein.

9. A vascular device for treating a target site within a body lumen comprising:
   a primary tubular structure comprising a wall defining a first end, a second end, and a primary lumen extending between the first and second ends;
   a secondary tubular structure disposed within the primary lumen of the primary tubular structure, wherein part of the wall defining the primary tubular structure comprises a wall extension that extends into the primary lumen to define the secondary tubular structure, wherein the secondary tubular structure comprises a secondary lumen, wherein the secondary tubular structure is configured to receive an endograft via the secondary lumen and is configured to serve as a landing zone for the endograft, and wherein at least a portion of an outer surface of the wall extension of the secondary tubular structure is spaced from an inner surface of the primary tubular structure and defines a chamber therebetween; and
   at least one debranching limb extending from a portion of the primary tubular structure defined by the wall in the area of the chamber, opposite the wall extension, such that blood is able to through each debranching limb via the chamber to a corresponding branch vessel and is able to flow through the secondary lumen to points downstream,
   wherein at least one of the first or second ends of the primary tubular structure comprises an inner skirt and an outer skirt configured to receive a portion of a respective section of a native blood vessel therebetween for attaching the respective end of the primary tubular structure to the respective section of the native blood vessel.

10. The vascular device of claim 9, wherein a portion of the secondary tubular structure is integral to the primary tubular structure.

11. The vascular device of claim 9, wherein at least a portion of the secondary tubular structure comprises a nitinol mesh.

* * * * *